(12) United States Patent
Kosmeder et al.

(10) Patent No.: US 8,263,361 B2
(45) Date of Patent: Sep. 11, 2012

(54) STABILIZED HEMATOXYLIN

(75) Inventors: Jerome W. Kosmeder, Tucson, AZ (US); Christopher Bieniarz, Tucson, AZ (US); Penny Towne, Tucson, AZ (US); Linda Willoughby Kivi, Marana, AZ (US)

(73) Assignee: Ventana Medical Systems, Inc., Tucson, AZ (US)

( * ) Notice: Subject to any disclaimer, the term of this patent is extended or adjusted under 35 U.S.C. 154(b) by 1216 days.

(21) Appl. No.: 12/048,749

(22) Filed: Mar. 14, 2008

(65) Prior Publication Data

US 2008/0227143 A1   Sep. 18, 2008

Related U.S. Application Data

(60) Provisional application No. 60/895,007, filed on Mar. 15, 2007.

(51) Int. Cl.
*G01N 1/30* (2006.01)
(52) U.S. Cl. .................... 435/40.52; 435/40.5
(58) Field of Classification Search .................. None
See application file for complete search history.

(56) References Cited

U.S. PATENT DOCUMENTS

| | | | |
|---|---|---|---|
| 4,502,864 A | 3/1985 | Cleverdon | |
| 4,816,244 A | 3/1989 | Starkweather | |
| 4,837,331 A | 6/1989 | Yamanishi et al. | |
| 5,108,505 A | 4/1992 | Moffatt | |
| 5,296,472 A * | 3/1994 | Sanchez et al. | 514/58 |
| 5,679,573 A | 10/1997 | Williams et al. | |
| 5,772,699 A | 6/1998 | Boyer | |
| 5,788,754 A | 8/1998 | Deardurff et al. | |
| 5,885,337 A | 3/1999 | Nohr et al. | |
| 6,764,540 B2 | 7/2004 | Taguchi | |
| 7,760,614 B2 * | 7/2010 | Peters et al. | 369/275.1 |
| 7,915,432 B2 * | 3/2011 | Foster | 549/383 |
| 2003/0163879 A1 | 9/2003 | Brennan et al. | |
| 2004/0002163 A1 | 1/2004 | Reinhardt et al. | |
| 2005/0186114 A1 | 8/2005 | Reinhardt et al. | |
| 2008/0139827 A1 | 6/2008 | Foster | |

FOREIGN PATENT DOCUMENTS

| | | |
|---|---|---|
| EP | 0 985 929 A1 | 3/2000 |
| EP | 1 048 289 A2 | 11/2000 |
| EP | 1 331 252 A2 | 7/2003 |
| JP | 59051279 | 3/1984 |
| JP | 02-205773 A | 8/1990 |
| JP | 04202119 | 7/1992 |
| JP | 05-130890 A | 5/1993 |
| JP | 08-301298 A | 11/1996 |
| JP | 03-072414 A | 3/1997 |
| JP | 2000-187033 A | 7/2000 |
| JP | 2004-359783 A | 12/2004 |
| JP | 2005-060293 A | 3/2005 |
| WO | WO 91/05605 | 5/1991 |
| WO | WO 2004/032862 A2 | 4/2004 |
| WO | 2005/034937 A1 | 4/2005 |
| WO | WO 2006/006969 A1 | 1/2006 |

* cited by examiner

*Primary Examiner* — Hope Robinson
(74) *Attorney, Agent, or Firm* — Ventana Medical Systems, Inc.

(57) ABSTRACT

A stabilized hematoxylin composition is disclosed that includes one or both of a host compound and an antioxidant. The disclosed composition exhibits sufficient stability to be utilized in an automated staining process without undue degradation prior to use of the composition to stain a biological sample. Methods of using and making the stabilized composition also are disclosed.

33 Claims, 3 Drawing Sheets

STABILIZED HEMATOXYLIN

RELATED APPLICATION DATA

This claims the benefit of U.S. Provisional Patent Application No. 60/895,007, filed Mar. 15, 2007, which application is incorporated by reference herein.

FIELD

The present invention relates to a composition and method for histochemical staining of biological samples. More particularly, the present invention relates to a dye formulation that is stabilized against degradation over time, and use of the formulation to stain biological samples.

BACKGROUND

Several histochemical staining protocols, including Hematoxylin and Eosin (H&E) staining and Papanicolaou (PAP) staining, rely on the dye hematoxylin to stain cytological and tissue samples. In particular, hematoxylin staining of cell nuclei is used by pathologists to detect the presence of malignant and/or metastatic cells in a tumor biopsy sample.

Hematoxylin is a naturally-occurring compound found in the red heartwood of trees of the genus *Hematoxylon*. Hematoxylin itself is colorless in aqueous solution and is not the active ingredient that stains tissue components. Rather, an oxidation product of hematoxylin, hematein, becomes the active staining component of a hematoxylin dye solution, particularly upon complexation with a mordant. Hematein is produced naturally through exposure to air and sunlight. The natural process is termed "ripening," and can take 3 or more months to provide a solution suitable for staining cells.

In order to accelerate the conversion of hematoxylin to hematein, a chemical oxidant can be utilized. Unfortunately, the accelerated process often produces ineffective reaction products such as oxyhematein and complex polymeric precipitates, and also provides a solution that degrades faster than a naturally ripened dye solution. The exact amount of oxidant needed to quantitatively oxidize hematoxylin to hematein can be used to help avoid over-oxidation to ineffective products, but a partially-oxidized solution is more typically utilized when staining is not performed immediately. In a partially-oxidized solution, natural oxidation of the hematoxylin that is remaining after a chemical oxidation step will continue to replace any hematein that is either consumed during staining or is naturally oxidized further to ineffective products. Still, the concentration (and amount) of hematein can change over time.

Since hematein is the active staining component of a hematoxylin solution, changes in its concentration (and/or the concentration of its mordant complexes) over time leads to staining inconsistencies. In a manual staining procedure, changes in hematein content of a hematoxylin solution can be compensated for by altering the contact time of a biological sample with the solution based on visual inspection. For example, an apparently under-stained sample can simply be placed back into the hematoxylin solution for a period of time to increase the staining intensity. In an automated staining procedure, however, "visual" inspection and extension of the exposure time in response to under-staining can require costly imaging equipment and can disrupt processing of other samples. Therefore, a need exists for a hematoxylin solution wherein the concentration of hematein available for staining is better stabilized over time.

SUMMARY

In one aspect, a stabilized hematoxylin composition is disclosed. In one embodiment, the composition includes: a solvent; hematoxylin; an amount of a chemical oxidant sufficient to convert at least a portion of the hematoxylin to hematein; a mordant; and either or both of a host compound and an antioxidant. In a particular embodiment, a disclosed hematoxylin solution includes hematoxylin, water, a polyol, an amount of an oxidant sufficient to convert at least a portion of the hematoxylin to hematein, a mordant, and either or both of an antioxidant and a host compound.

In another aspect, a method is disclosed for histochemical staining of a biological sample. The method includes contacting the biological sample with a disclosed hematoxylin composition, and can further include contacting the sample with one or more additional staining compositions, such as one or more counter-stains. In a particular embodiment, the method further includes contacting the sample with an eosin composition. In another particular embodiment, the method is automated.

Also disclosed is a method for making a stabilized hematoxylin composition that can be used for histochemical staining of a biological sample. In one embodiment, the method includes forming a hematein solution, adding a mordant to the hematein solution to form a staining solution, and adding either or both of a host compound and an antioxidant to the staining solution to form the stabilized hematoxylin composition. The hematein solution can be formed by dissolving hematein directly in a solvent, by dissolving hematoxylin in a solvent and then adding a chemical oxidant to convert at least a portion of the hematoxylin into hematein, or by a combination of dissolution of hematein and conversion of hematoxylin to hematein.

DETAILED DESCRIPTION OF SEVERAL ILLUSTRATIVE EMBODIMENTS

The following description of several embodiments describes non-limiting examples that further illustrate the invention. All titles of sections contained herein, including those appearing above, are not to be construed as limitations on the invention, but rather are provided to structure the illustrative description of the invention that is provided by the specification. In order to aid the reader in understanding the various illustrated embodiments, explanations of particular terms utilized in the description are provided, after which an overview of particular embodiments of the invention and specific examples are provided.

I. Terms

Unless defined otherwise, all technical and scientific terms used herein have the same meanings as commonly understood by one skilled in the art to which the disclosed invention pertains.

The singular forms "a," "an," and "the" include plural referents unless the context clearly indicates otherwise. Thus, for example, reference to "a host compound" refers to one or more host compounds, such as 2 or more host compounds, 3 or more host compounds, or even 4 or more host compounds.

The term "antioxidant" refers to an atom or molecule that has a greater oxidation potential than a second atom or molecule, such that the antioxidant is preferentially oxidized instead of the second atom or molecule. For example, an antioxidant can have a greater oxidation potential than hematein, and thus help prevent oxidation of hematein to oxyhematein. Furthermore, an antioxidant also can function as a reducing agent, for example, a reducing agent that converts oxyhematein back to hematein. Antioxidants can be present in the disclosed compositions at concentrations ranging from about 1 mM to about 1M, for example, from about 5 mM to about 500 mM, such as from about 50 mM to about 150 mM.

The term "aqueous solvent" refers to a composition having water as the major component and that is a liquid at room temperature. Mixtures of water and one or more lower alkanols or polyols that have 50% or greater water content by volume are examples of aqueous solvents.

The term "biological sample" refers to any sample that is obtained from or otherwise derived from a biological entity such as an animal, for example, a sample obtained from a human or a veterinary animal such as a dog, cat, horse or cow. Examples of biological samples include cytology samples, tissue samples and biological fluids. Non-limiting particular examples of biological samples include blood, urine, pre-ejaculate, nipple aspirates, semen, milk, sputum, mucus, pleural fluid, pelvic fluid, sinovial fluid, ascites fluid, body cavity washes, eye brushings, skin scrapings, a buccal swab, a vaginal swab, a pap smear, a rectal swab, an aspirate, a needle biopsy, a section of tissue obtained for example by surgery or autopsy, plasma, serum, spinal fluid, lymph fluid, sweat, tears, saliva, tumors, organs and samples obtained from in vitro cell or tissue cultures. Typically, the sample will be a biopsy sample that has been fixed, processed to remove water and embedded in paraffin or another suitable waxy substance for cutting into tissue sections. Biological samples can be mounted on substrates such as microscope slides for treatment and/or examination.

The term "hematoxylin composition," as used herein, generically refers both to compositions formed by dissolving hematein (the oxidation product of hematoxylin) directly into a solvent and to compositions formed by dissolving hematoxylin in a solvent and allowing or promoting oxidation of the hematoxylin to hematein. Although it is more typical to prepare the disclosed compositions by dissolving hematoxylin in a solvent and converting the hematoxylin to hematein (either completely or partially) by natural oxidation through contact with air or accelerated chemical oxidation, the benefits of the stabilizing effects of the disclosed composition components can also be utilized in combination with hematein compositions prepared by directly dissolving hematein in solvent. Thus, in some embodiments, a "hematoxylin composition" will include, at least initially, little or no hematoxylin, and consist primarily of hematein.

The term "host compound" refers to an organic or inorganic molecule, complex or material having an inner cavity portion or groove portion, and more particularly, to a molecule having an inner cavity portion or groove portion that can accommodate at least a portion of a hematein or other dye molecule. Host compounds include polysaccharides such as amyloses, cyclodextrins and other cyclic or helical compounds containing a plurality of aldose rings, for example, compounds formed through 1,4 and 1,6 bonding of monosaccharides (such as glucose, fructose, and galactose) and disaccharides (such as saccharose, maltose, and lactose). Other host compounds include cryptands, cryptophanes, cavitands, crown ethers, dendrimers, nanotubes, calixarenes, valinomycins, and nigericins. In particular embodiments, a host compound can be a cyclodextrin or cyclodextrin derivative, and more particularly, a host compound can be a cyclodextrin or cyclodextrin derivative exhibiting water solubility at 25° C. of greater than 5 mg/mL, such as greater than 20 mg/mL, greater than 100 mg/mL, or even greater than 500 mg/mL. In other particular embodiments, a host compound can be $\alpha$-amylose, $\beta$-amylose or V-amylose. Host compounds can be included at concentrations ranging from about 1 mM to about 1M, for example, from about 5 mM to about 500 mM, such as from about 5 mM to about 25 mM.

Host compounds can include cyclodextrin derivatives, amylose derivatives, cryptand derivatives, cryptophane derivatives, cavitand derivatives, crown ether derivatives, dendrimer derivatives, nanotube derivatives, calixarene derivatives, valinomycin derivatives, and nigericin derivatives modified with one or more substituents. For example, host compounds include amylose derivatives and cyclodextrin derivatives, wherein one or more of the hydroxyl groups or the hydrogen atoms of the hydroxyl groups of their constituent aldose rings are replaced with substituents. Examples of substituents include acyl groups (such as acetyl groups), alkyl groups, aryl groups, tosyl groups, mesyl groups, amino groups (including primary, secondary, tertiary and quaternary amino groups), halo groups (—F, —Cl, —Br and —I), nitro groups, phosphorous-containing groups (such as phosphate and alkylphosphate groups), sulfur-containing groups (such as sulfate and sulfate ester groups), bridging groups, (that, for example, connect two or more hydroxyl positions on a cyclodextrin ring or connect two or more host compounds), aldehyde groups, ketone groups, oxime groups, carboxylic acid groups and their derivatives, carbonate and carbamate groups, silicon-containing groups, boron-containing groups, tin-containing groups, and hydroxyalkyl groups (such as hydroxyethyl groups and hydroxypropyl groups).

Particular examples of cyclodextrins include $\alpha$-cyclodextrin, $\beta$-cyclodextrin, $\gamma$-cyclodextrin, and $\delta$-cyclodextrin, and derivatives of each of these classes of cyclodextrins. Particular examples of cyclodextrin derivatives, include hydroxypropylated $\alpha$-cyclodextrin, hydroxypropylated $\beta$-cyclodextrin, hydroxypropylated $\gamma$-cyclodextrin, hydroxyethylated $\alpha$-cyclodextrin, hydroxyethylated $\beta$-cyclodextrin, hydroxyethylated $\gamma$-cyclodextrin, hydroxyisopropylated $\alpha$-cyclodextrin, hydroxyisopropylated $\beta$-cyclodextrin, hydroxyisopropylated $\gamma$-cyclodextrin, carboxymethylated $\alpha$-cyclodextrin, carboxymethylated $\beta$-cyclodextrin, carboxymethylated $\gamma$-cyclodextrin, carboxyethylated $\alpha$-cyclodextrin, carboxyethylated $\beta$-cyclodextrin, carboxyethylated $\gamma$-cyclodextrin, octyl succinated-$\alpha$-cyclodextrin, octyl succinated-$\beta$-cyclodextrin, octyl succinated-$\gamma$-cyclodextrin, acetylated-$\alpha$-cyclodextrin, acetylated-$\beta$-cyclodextrin, acetylated-$\gamma$-cyclodextrin, sulfated-$\alpha$-cyclodextrin, sulfated-$\beta$-cyclodextrin and sulfated-$\gamma$-cyclodextrin. Other particular examples of cyclodextrins derivatives include the following $\beta$-cyclodextrin derivatives: 2,3-dimethyl-6-aminomethyl-$\alpha$-cyclodextrin, 6-Azido-$\alpha$-cyclodextrin, 6-Bromo-$\beta$-cyclodextrin, 6A,6B-dibromo-$\beta$-cyclodextrin, 6A,6B-diiodo-$\beta$-cyclodextrin, 6-O-Maltosyl-$\beta$-cyclodextrin, 6-Iodo-$\alpha$-cyclodextrin, 6-Tosyl-$\beta$-cyclodextrin, Peracetyl-maltosyl-$\beta$-cyclodextrin, 6-t-butyldimethylsilyl-$\beta$-cyclodextrin, 2,3-diacetyl-6-butyldimethylsilyl-$\beta$-cyclodextrin, 2,6-dibutyl-3-acetyl-$\beta$-cyclodextrin, 2,6-dibutyl-$\beta$-cyclodextrin, 2,6-t-butyl-dimethylsilyl-$\beta$-cyclodextrin, and 2,6-di-O-methyl-3-allyl-$\beta$-cyclodextrin. A variety of cyclodextrins and cyclodextrin derivatives can be obtained commercially, for example, from CTD, Inc. (High Springs, Fla.), or they can be synthesized according to procedures outlined in the scientific literature, for example, in "Synthesis of Chemically Modified Cyclodextrins," Croft and Bartsch, *Tetrahedron*, 39: 1417-1474, 1983.

The term "lower alkanol" refers to a compound having the formula R—OH, where R is an alkyl group having between 1 and 5 carbon atoms such as a methyl group, an ethyl group, an n-propyl group, an isopropyl group, an n-butyl group, a sec-butyl group, a t-butyl group, an n-pentyl group, an isopentyl group or a neopentyl group. Examples of lower alkanols include methanol, ethanol and isopropanol.

The term "oxidant" refers to an atom or molecule having a greater reduction potential than a second molecule, for example, a greater reduction potential than hematoxylin such that it will react with and oxidize hematoxylin to hematein. Oxidants include naturally occurring molecular oxygen in the atmosphere that diffuses to and oxidizes hematoxylin and a "chemical oxidant" that is actively combined with hematoxylin (typically in solution) to convert at least a portion of the hematoxylin to hematein. Examples of useful chemical oxidants include one or more of an iodate salt (such as sodium iodate and potassium iodate), mercuric oxide, a permanganate salt (such as potassium permanganate), a periodate salt (such as sodium periodate and potassium periodate), and a peroxide (such as hydrogen peroxide). In particular embodiments, the chemical oxidant comprises sodium iodate.

The term "mordant" refers to an ionic metal species with which a dye (such as hematein) can form a complex (such as a cationic complex) that serves to bind the dye (such as hematein) to particular cellular components such as nuclear DNA, myelin, elastic and collagen fibers, muscle striations and mitochondria. Examples of mordants include aluminum (for example, in the form of an alum such as aluminum sulphate, aluminum potassium sulphate or aluminum ammonium sulphate), iron, tungsten, zirconium, bismuth, molybdenum (phosphomolybdic acid or molybdic acid), vanadium (vanadate).

The term "water-soluble antioxidant" refers to an antioxidant that has a solubility in water at 25° C. that is sufficient to provide a concentration of the antioxidant of at least 1 mM, such as greater than 5 mM, greater than 10 mM, or even greater than 50 mM.

II. Overview

A stabilized hematoxylin composition is disclosed, which composition can be used for staining of a biological sample, and in particular, for staining the nuclei of cells in the biological sample. The composition includes mordanted hematein (such as hemalum) stabilized by one or both of a host compound and an antioxidant. The disclosed hematoxylin compositions show improved stability over similar hematoxylin compositions not including either or both of a host compound and an antioxidant. Likewise, the use of antioxidants and host compounds to increase stability of other histochemical dye compositions and their use in histochemical staining methods are contemplated. Furthermore, in the case of hematoxylin, a disclosed hematoxylin composition also appears to have a higher effective dye concentration that permits darker staining of biological samples in a predetermined amount of time, which is especially advantageous in an automated staining method where a biological sample mounted on a microscope slide, and even more advantageous if the slide is processed in a horizontal position. All known hematoxylin compositions and all histochemical staining methods utilizing hematoxylin as part of the staining process can benefit from application of the teachings of the present disclosure. Furthermore the benefits can be extended to "special stains" and the automated application of such special stains to biological samples (such as on the NexES™ Special Stainer (Ventana Medical Systems, Inc., Tucson, Ariz.).

In one embodiment, the disclosed composition includes hematoxylin, a solvent, an amount of a chemical oxidant sufficient to convert at least a portion of the hematoxylin to hematein, a mordant and either or both of a host compound and an antioxidant. In particular embodiments, the composition includes both a host compound and an antioxidant. In even more particular embodiments, the composition includes two or more different antioxidants such as two or more water-soluble antioxidants. In other even more particular embodiments, the composition includes one or more host compounds and one or more antioxidants.

The host compound of various embodiments can be one or more of an amylose, a cyclodextrin, a cryptand, a cryptophane, a cavitand, a crown ether, a dendrimer, a nanotube, a calixarene, a valinomycin, and a nigericin. In more particular embodiments, the host compound is one or more of a cyclodextrin or a cyclodextrin derivative, and more particularly one or more of β-cyclodextrin and a β-cyclodextrin derivative. In other more particular embodiments, the host compound can have a water solubility of greater than 100 mg/mL at 25° C.

In some embodiments, the solvent is an aqueous solvent and the antioxidant is a water-soluble antioxidant. Examples of water soluble antioxidants include hydroquinones; n-alkyl gallates (such as n-propyl, n-octyl, and n-dodecyl gallates); reducible sugars such as sorbitol and mannitol; benzoates and hydroxybenzoates; sulfites and metabisulfites; certain acids such as citric acid, tartaric acid, lactic acid, erythorbic acid ascorbic acid, uric acid, tannic acid, and salts of such acids (such as $Mg^{2+}$, $NH_4^+$, $Na^+$, $K^+$ and $Ca^{2+}$ salts); chelators such as EDTA that remove metals that function as oxidants; and choral hydrate. In particular embodiments, the water soluble antioxidant includes one or more of hydroquinone and n-propyl gallate.

Various solvents can be utilized for the composition, but typically the solvent comprises one or more of water, a lower alkanol such as ethanol, and a polyol. In particular embodiments, the solvent comprises an aqueous solvent wherein the aqueous solvent comprises water and a polyol. Particular examples of useful polyols include glycerol, ethylene glycol, propylene glycol, poly (ethylene glycol), and poly (propylene glycol). Aqueous solvent compositions typically will comprise 5-45% by volume of one or more of ethylene glycol and propylene glycol, and more typically 10-30% by volume of one or more of ethylene glycol and propylene glycol.

The amount of chemical oxidant utilized in some embodiments of the composition can be sufficient to completely (such as substantially quantitatively) oxidize the hematoxylin to hematein, or sufficient only to partially oxidize the hematoxylin to hematein. In particular embodiments, more than half of the hematoxylin is oxidized to hematein by the chemical oxidant, and in others, less than half of the hematoxylin is oxidized to hematein by the chemical oxidant. For example, between 1% and 50% of the hematoxylin can be oxidized to hematein by the chemical oxidant, but more typically, between about 10% and about 30% of the hematoxylin is oxidized to hematein by the chemical oxidant. In particular examples, the molar ratio of hematoxylin to oxidant used in the composition is between 6:1 and 1:1. It should be understood that although the chemical oxidant is considered part of the composition, it is converted to its reduction products upon reaction with the hematoxylin, which reduction products will remain in the composition.

The mordant of the composition can be any mordant such as one or more of an aluminum mordant, an iron mordant, a bismuth mordant, a copper mordant, a molybdenum mordant, a vanadium mordant, and a zirconium mordant. In some embodiments, the mordant comprises an alum, and in more particular embodiments, the mordant comprises aluminum sulphate. The mordant can be present in the composition at a concentration greater than the concentration of the hematein in the composition (determinable by refractometry, thin-layer chromatography or spectroscopy), or it can be present in the composition at a concentration less than the concentration of the hematein in the composition. Alternatively, in some embodiments, the molar ratio of hematoxylin to mordant in the composition is between 2:1 and 1:100, and in particular embodiments, the molar ratio of hematoxylin to mordant in the composition is between 1:5 and 1:20.

In some embodiments, the composition further includes an acid such as acetic acid. In other embodiments, no acid is added, and the absence of the acid surprisingly still provides a stabilized and effective hematoxylin composition. In other embodiments, the composition further includes a buffer to control pH, for example, a buffer to control the pH near a pH between 1 and 4, such as a pH near 2.5.

In some particular embodiments, a disclosed composition comprises a mixture of water and ethylene glycol as the solvent, sodium iodate as the oxidant, aluminum sulphate as the mordant, and β-cyclodextrin or a derivative thereof as the host compound. One or more water soluble antioxidants such as hydroquinone and n-propyl gallate also can be included in such particular embodiments. In even more particular embodiments, the mixture of water and ethylene glycol comprises from 10-40% by volume ethylene glycol and from 60-90% water.

In another aspect, a method is disclosed for histochemical staining of a biological sample, which method includes contacting the biological sample with a disclosed hematoxylin composition and can further include contacting the sample with a counterstain. In some embodiments, contacting the sample with a counterstain comprises contacting the sample with one or more of eosin Y, orange G, light green SF yellowish, Bismark Brown, fast green FCF, OA-6, EA25, EA36, EA50 and EA65. The formulas and methods of making such counterstains can be found, for example, in the StainsFile (an internet resource for histotechnologists maintained by Bryan Llewellyn); Kiernan, "Histological and Histochemical methods: Theory and Practice," $3^{rd}$ Ed. Butterworth Heinemann, Oxford, UK; and in Horobin and Kiernan, "Conn's biological stains: a handbook of dyes, stains and fluorochromes for us in biology and medicine," $10^{th}$ ed., Oxford: BIOS, ISBN 1859960995, 2002. In other embodiments, contacting the sample with the hematoxylin composition comprises a progressive hematoxylin staining protocol. In yet others, contacting the sample with the hematoxylin composition comprises a regressive hematoxylin staining protocol. The method can be automated, and can be performed on a biological sample that is supported on a substrate such as a microscope slide. In particular embodiments, the method is used to stain a tissue section or a cytology sample mounted on a microscope slide. In particular embodiments further including a counterstaining step, the method can be an H&E staining method or a PAP staining method, and more particularly an automated H&E or PAP staining method.

In a further aspect, a method is disclosed for making a stabilized hematoxylin composition for histochemical staining of a biological sample. In one embodiment, the method for making the stabilized hematoxylin solution includes forming a hematein solution, adding a mordant to the hematein solution to form a staining solution, and adding either or both of a host compound and an antioxidant to the staining solution to form the stabilized hematoxylin composition. In some embodiments, forming the hematein solution comprises dissolving hematoxylin in a solvent and adding an amount of a chemical oxidant sufficient to covert at least a portion of the hematoxylin to hematein. In particular embodiments, the solvent used to dissolve the hematoxylin comprises an aqueous composition such as composition including water and a polyol. Useful polyols, as indicated before, include glycerol, ethylene glycol and propylene glycol.

While the principles outlined in this disclosure are applied to variants of Gill's mordanted hematoxylin in the examples that follow, it should be understood that they can be applied to improve the stability of any mordanted hematoxylin used for histochemical staining of biological samples. In addition to Gill's formulations, particular examples of alum mordanted hematoxylin histological stains to which a host compound and/or an antioxidant can be added to improve stability include Anderson's, Apathy's, Baker's Bennett's, Bohmer's, Bosma's, Bullard's, Carazzi's, Cole's, Debiden's, de Groot's, Delafield's, Duval's, Ehrlich's, Friedlander's, Gadsdon's, Gage's, Galigher's, Garvey's, Graham's, Hamilton's, Harris', Harris & Power's, Haug's, Horneyold's, Kleinenberg's, Krutsay's, Langeron's, Launoy's, Lee's, Lillie's, Lugol's, McLachlan's, Mallory's, Mann's, Martinotti's, Masson's, Mayer's, Mitchell's, Molnar's, Papamiltiades', Pusey's, Rawitz', Reddy's, Sass', Schmorl's, Slidders', Unna's, Watson's, and Weigert & Wright's. Particular examples of iron-mordanted hematoxylin stains include Anderson's, Cretin's, Faure's, Goldman's, Hansen's, Heidenhain's, Janssen's, Kefalas', Krajian's, Krutsay's, La Manna's, Lillie's, Lillie & Earle's, Masson's, More & Bassal's, Murray's, Paquin & Goddard's, Regaud's, Rozas', Seidelin's, Thomas', Weigert's, and Yasvoyn's. A bismuth-mordanted hematoxylin is Roach & Smith's. Copper-mordanted hematoxylins include Bensley's, Cook's and Faure's. A molybdenum-mordanted hematoxylin is Held's. Vanadium-mordanted hematoxylins include Hedenhain's, and Smith's. A zirconium-mordanted hematoxylin is McNulty & Smith's. Formulas and methods of making and using such mordanted hematoxylin solutions can be found, for example, in the StainsFile (an internet resource for histotechnologists maintained by Bryan Llewellyn); Kiernan, "Histological and Histochemical methods: Theory and Practice," $3^{rd}$ Ed. Butterworth Heinemann, Oxford, UK; and in Horobin and Kiernan, "Conn's biological stains: a handbook of dyes, stains and fluorochromes for us in biology and medicine," $10^{th}$ ed., Oxford: BIOS, ISBN 1859960995, 2002. The contents of the two bound references cited immediately above are incorporated by reference herein.

Other histological stains and their methods of use (particularly automated methods of use) that can benefit from the stabilizing effects of one or more of an antioxidant and a host compound include dyes such as acridine dyes, anthraquinone dyes, arylmethane dyes, azo dyes, diazonium dyes, nitro dyes, phthalocyanine dyes, quinine imine dyes, tetrazolium dyes, thiazole dyes and xanthene dyes. Examples of dyes useful for histological staining include acetyl yellow, acid black 1, acid blue 22, acid blue 93, acid fuchsin, acid green, acid green 1, acid green 5, acid magenta, acid orange 10, acid red 4, acid red 26, acid red 29, acid red 44, acid red 51, acid red 66, acid red 73, acid red 87, acid red 91, acid red 92, acid red 94, acid red 101, acid red 103, acid roseine, acid rubin, acid violet 19, acid yellow 1, acid yellow 9, acid yellow 23, acid yellow 24, acid yellow 36, acid yellow 73, acid yellow S, acid yellow T, acridine orange, acriflavine, alcian blue, alcian yellow, alcohol soluble eosin, alizarin, alizarin blue, alizarin blue 2RC, alizarin carmine, alizarin cyanin BBS, alizarol cyanin R, alizarin red S, alizarin purpurin, aluminon, amido black 10B, amidonaphthol red, amidoschwarz, aniline blue WS, aniline purple, anthracene blue SWR, anthracene blue SWX, auramine 0, azo-eosin, azocarmine B, azocarmine G, azoeosin G, azoic diazo 5, azoic diazo 48, azophloxine, azovan blue, azure A, azure B, azure C, basic blue 8, basic blue 9, basic blue 12, basic blue 15, basic blue 17, basic blue 20, basic blue 26, basic brown 1, basic fuschsin, basic green 4, basic green 5, basic orange 14, basic red 2, basic red 5, basic red 9, basic violet 2, basic violet 4, basic violet 10, basic violet 14, basic yellow 1, basic yellow 2, Biebrich scarlet, Biebrich scarlet R, Bismarck brown Y, brazilein, brazilin, brilliant crocein, brilliant crystal scarlet 6R, calcium red, carmine, carminic acid carmoisine 6R, Celestine blue B, china blue, chlorantine fast red 5B, cochineal, coelestine blue, Chicago blue 4B, chrome violet CG, chromotrope 2R, chromoxane cyanin R, congo Corinth, Congo red, cotton blue cotton red, croceine scarlet crocein scarlet 3B, crocein scarlet MOO, crocin, crystal ponceau 6R, crystal scarlet, crystal violet, dahlia, diamond green B, direct blue 14, direct blue 58, direct red, direct red 10, direct red 28, direct red 80, direct red 81, direct yellow 7, durazol blue 4R, durazol blue 8G, eosin B, eosin bluish, eosin, eosin Y, eosin yellowish, eosinol, Erie garnet B, eriochrome cyanin R, erythrosine B ethyl eosin, ethyl green, ethyl violet, Evan's blue, fast blue B, fast green FCF, fast red B, fast yellow, fast yellow extra, fast yellow G, fat black HB, fluorescein, food green 3, galleon, gallamine blue gallocyanin, gentian violet, helio fast rubin BBL, helvetia blue, Hoffman's violet, hydrazine yellow, imperial red, ingrain blue 1, ingrain yellow 1, INT, Kermes, kermesic acid, kemechtrot, Lac, laccaic acid, Lauth's violet, light green, lissamine fast yellow, lissamine green SF, Luxol fast blue, magenta 0, magenta I, magenta II, magenta III, malachite green, Manchester brown, Martius yellow, mauve, mauveine, merbromin, mercurochrome, metanil yellow, methylene azure A, methylene azure B, methylene azure C, methylene blue, methylene green, methyl blue, methyl green, methyl violet, methyl biolet 2B, methyl violet 10B, milling yellow 3G, mordant blue 3, mordant blue 10, mordant blue 14, mordant blue 23, mordant blue 32, mordant blue 45, mordant red 3, mordant red 11, mordant violet 25, mordant violet 39, naphthalene blue black, naphthol blue black, naphthol green B, naphthol yellow S, natural black 1, natural red, natural red 3, natural red 4, natural red 8, natural red 16, natural red 24, natural red 25, natural red 28, natural yellow 6, NBT, neutral red, new fuchsin, Niagara blue 3B, night blue, Nile blue, Nile blue A, Nile blue sulfate, Nile red, nitro BT, nitro blue tetrazolium, nuclear fast red, oil red O, orange G, orcein, pararosanilin, Perkin's violet, phloxine B, picric acid, Ponceau 2R, Ponceau 6R, Ponceau B, Ponceau de Xylidine, Ponceau S, pontamine sky blue 5B, primula, primuline, purpurin, pyronin B, pyronin G, pyronin Y, rhodamine B, rosanilin, rose Bengal, saffron, safranin O, scarlet R scarlet red, Scharlach R, shellac, sirius red F3B, sirius red 4B, sirius supra blue F3R, solochrome cyanin R, soluble blue, solvent black 3, solvent blue 38, solvent red 23, solvent red 24, solvent red 27, solvent red 45, solvent yellow 94, spirit soluble eosin, Sudan III, Sudan IV, Sudan black B, Sudan red BK, sulfur yellow S, Swiss blue, tartrazine, thioflavine S, thioflavine T, thionin, toluidine blue, toluoyline red, tropaeolin G, trypaflavine, trypan blue, uranin, Vicoria blue 4R, Victoria blue B, Victoria blue R, Victoria green B, water blue I, water soluble eosin, woodstain scarlet, Xylidine ponceau, and yellowish eosin, and combinations thereof. Formulas and methods of making and using histochemical dye solutions discussed in this paragraph (such as in "special stain" procedures in particular histological contexts, or as counterstains) can be found, for example, in the StainsFile (an internet resource for histotechnologists maintained by Bryan Llewellyn); Kiernan, "Histological and Histochemical methods: Theory and Practice," $3^{rd}$ Ed. Butterworth Heinemann, Oxford, UK; and in Horobin and Kiernan, "Conn's biological stains: a handbook of dyes, stains and fluorochromes for us in biology and medicine," $10^{th}$ ed., Oxford: BIOS, ISBN 1859960995, 2002. The contents of the two bound references cited immediately above are incorporated by reference herein.

III. Examples

Although the method and composition of the disclosure can be applied to any histological staining process (manual or automated) or any slide staining instrument, the disclosed hematoxylin composition is particularly useful when incorporated into the automated H&E staining process developed for use in the high volume slide processing system that is described in U.S. Patent Application Publication Nos. 20040002163 and 20050186114 (both of which applications are incorporated by reference herein). Briefly, the automated slide processing system that is described in the aforementioned applications is a high-volume slide processing system that shuttles trays holding a plurality of slides in substantially horizontal positions (to minimize cross-contamination) between workstations that perform various slide processing operations on the slides. Fresh reagents can be applied to each slide during processing, and cross-contamination of slides with reagents can be substantially eliminated because the slides are treated separately in spaced-apart fashion in the tray. In one configuration, the system includes a radiant heater, a combined de-paraffinizer/stainer/solvent exchanger workstation, a convection oven and a coverslipper. A tray of slides bearing paraffin-embedded tissue samples can be heated under the radiant heater of the system to spread the paraffin in the samples for easier removal and also to adhere the samples to the slides. The tray can then be transported to the multifunctional de-paraffinizer/stainer/solvent exchanger workstation, where slides can be de-paraffinized, stained, and solvent exchanged. A tray of stained slides that is ready for coverslipping can then be shuttled to the coverslipper of the system where coverslips are added to the slides. Once the slides are coverslipped, the tray can then be transported to the convection oven to cure the coverslips on the stained slides. The high volume stainer just described is commercially available from Ventana Medical Systems, Inc, Tucson, Ariz.

Figure 1:
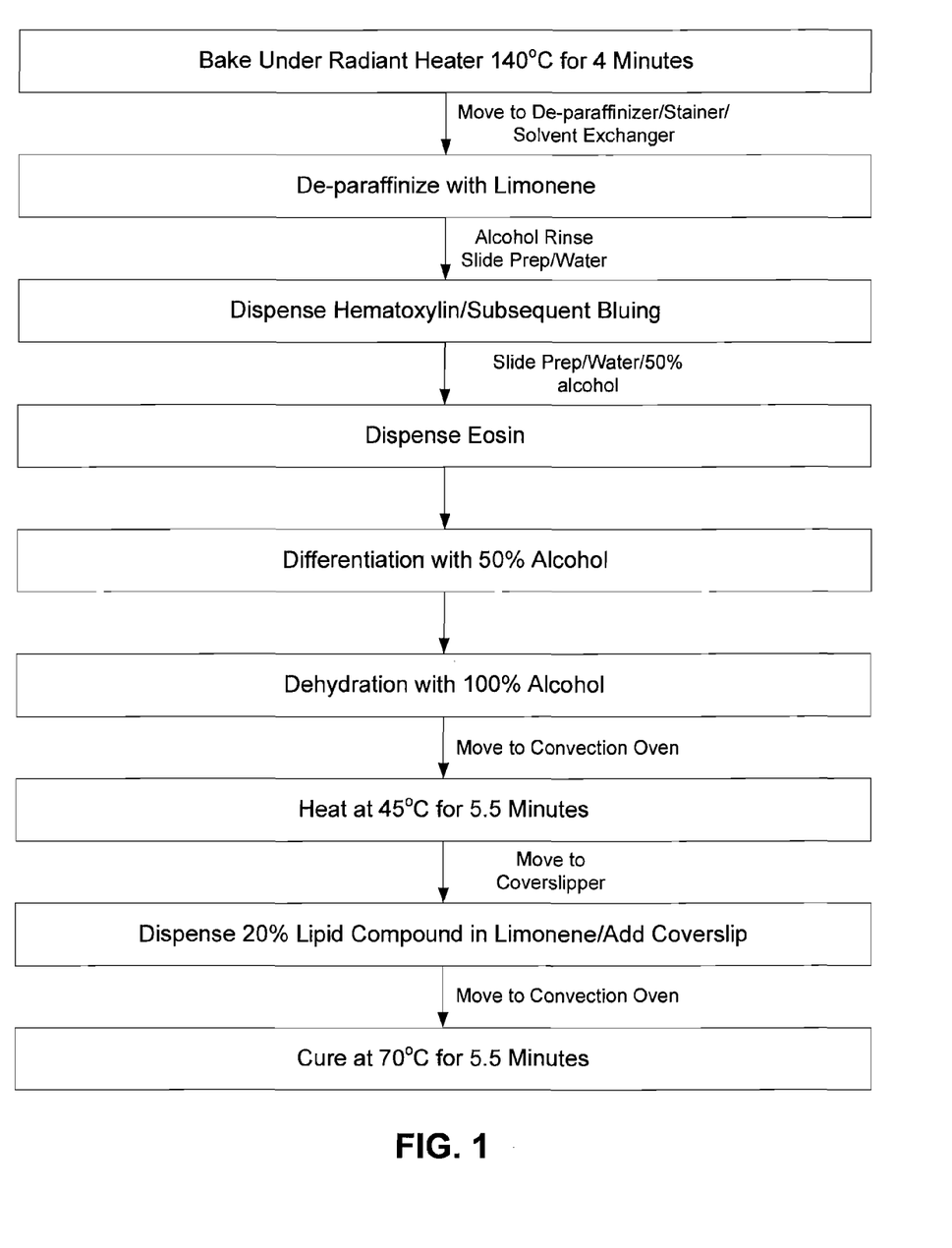
FIG. 1 is a block diagram outlining an automated H&E staining protocol into which the disclosed hematoxylin composition can be incorporated.

While the staining system just described can be configured to perform any histological staining process, the system was configured to perform a progressive H&E stain using the disclosed hematoxylin compositions that are described in detail below. A schematic showing the overall process is shown in FIG. 1, which process includes: a baking step to adhere the samples to the slides, a de-paraffinization step to remove paraffin from paraffin-embedded samples, a hematoxylin staining step (that can utilize the disclosed hematoxylin compositions), a bluing step that raises the pH and turns the hematoxylin blue to provide better contrast with the eosin added downstream, an eosin staining step, a differentiation step that is used to remove excess eosin and turn the eosin various shades of red to pink, a dehydration step to remove water from the sample using 100% ethanol, a step in which the slides are exposed to an elevated temperature and air flow to remove the ethanol, a coverslipping step in which limonene is dispensed to the sample, and a curing step.

Several hematoxylin compositions were investigated in an effort to provide a stable composition that also provided for a darker nuclear stain (by virtue of having a higher effective initial hematein concentration). Traditionally, solutions that have higher concentrations of hematein and that as a result can stain nuclei more darkly are made up and used within a few days because such solutions will form copious amounts of precipitate. Water-soluble antioxidants (in this example, hydroquinone and n-propyl gallate) were added to a variety of hematoxylin formulations, singly or in combination, to determine whether the antioxidants could stabilize the hematein against oxidative degradation and precipitation, and β-cyclodextrin was used to determine if addition of a host compound could further slow the natural oxidation of hematein and resulting precipitate formation.

In all instances, the hematoxylin formulations were prepared as follows:
1) Deionized water and either ethylene glycol (25% by volume; Sigma-Aldrich, St. Louis, Mo.) or propylene glycol (23% by volume; Sigma-Aldrich, St. Louis, Mo.) were mixed together to form a solvent for the composition.
2) Hematoxylin dye (Dudley Chemical Corp, Lakewood, N.J.), in the concentrations indicated in FIGS. 2 and 3, was then added to the solvent to form a hematoxylin solution.
3) Sodium iodate (Sigma-Aldrich, St. Louis, Mo.) was added in the concentrations indicated in FIGS. 2 and 3 and allowed to oxidize the hematoxylin to hematein, thereby forming a hematein solution having an initial molar concentration of hematein approximately equal to the molar concentration of the hematoxylin minus the molar concentration of the sodium iodate.
4) Aluminum sulphate octadecahydrate (JT Baker, Phillipsburg, N.J.) was added to the hematein solution in the concentration indicated in FIGS. 2 and 3 to form a hemalum solution.
5) Combinations of hydroquinone, n-propyl gallate and β-cyclodextrin hydrate (all available from Sigma-Aldrich, St. Louis, Mo.) were then added in the concentrations indicated in FIGS. 2 and 3 to form the tested compositions.
6) The compositions were placed into separate bag-in-box containers that are used for on-board storage of reagents in the automated staining system described above.

No acid was added to the compositions used for these examples.

Figure 2:
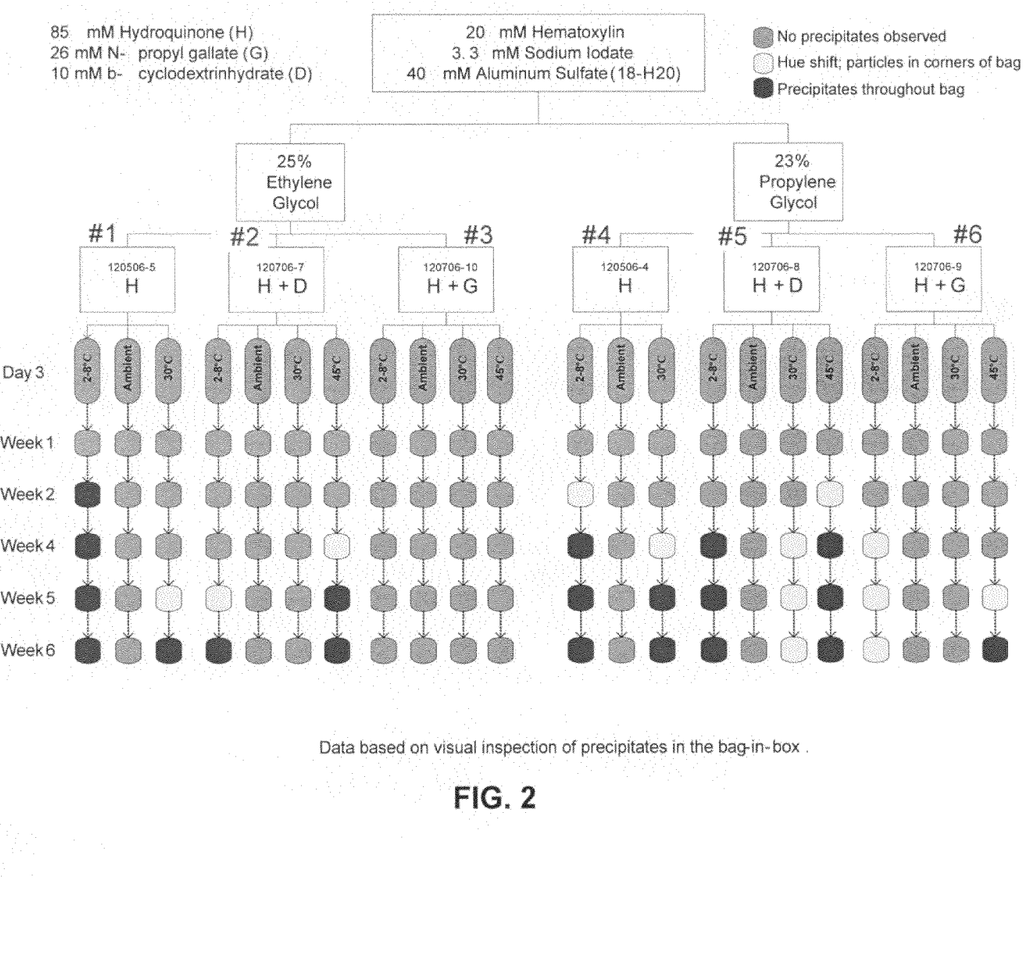
FIG. 2 is diagram showing stability results for several embodiments of the disclosed hematoxylin composition.
Figure 3:
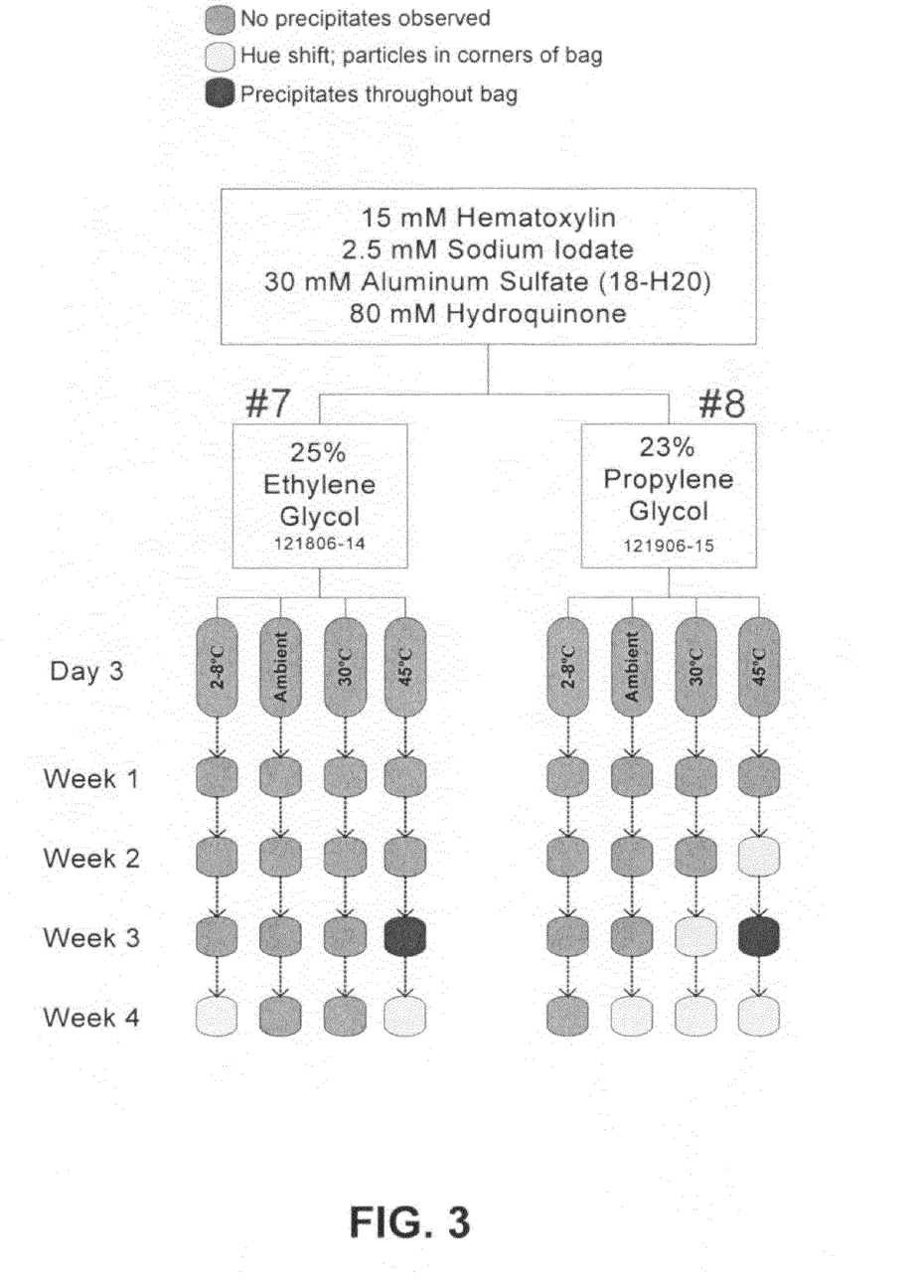
FIG. 3 is another diagram showing stability results for several embodiments of the disclosed hematoxylin composition.

FIGS. 2 and 3 summarize 8 different compositions and the results of stability testing at several temperatures based upon observation of precipitates in the bag-in-box containers. In all cases, the addition of one or more antioxidants and the host compound improved stability in comparison to an equivalent "unstabilized" hematoxylin solution without an added antioxidant and/or host compound, which unstabilized hematoxylin exhibits precipitates throughout the container after one week at 2-8° C., after 4 weeks at ambient temperature and at 30° C., and after 2 weeks at 45° C.

Long term stability testing that included use of stored compositions for manual staining of multi-tissue slides also was performed. Two lots of an aqueous hematoxylin solution including 25% ethylene glycol (v/v), 20 mM hematoxylin, 3.3 mM sodium iodate, 20 mM aluminum sulfate octadecahydrate, 85 mM hydroquinone and 10 mM β-cyclodextrin hydrate having a pH of about 2.6 were each packed into multiple bag-in-box containers. One container from each lot was left in ambient conditions, one container from each lot was subjected to freeze-thaw cycling, one container from each lot was subjected to 45 degrees C. to ambient ship stress conditions, and one container from each lot was subjected to 2-8 degrees C. to ambient ship stress conditions. At monthly intervals, each of the containers was inspected for the presence of precipitates and an aliquot was removed and checked for pH. The aliquot was then used to manually stain a microscope slide bearing multiple tissue sections (liver, kidney, colon, skin, and one of tonsil, lymph node or spleen). After a total of 13 months of monthly testing, the solutions in all of the different containers consistently did not exhibit precipitates, the pH of each of the solutions in the different containers consistently remained stable, and the hematoxylin solutions in the different containers consistently provided acceptable nuclear staining of the tissue sections following the manual staining procedure.

It is to be understood that the disclosed invention is not limited to the particular embodiments illustrated above and that many changes may be made without departing from the true scope and spirit of the invention. For example, additional components such as surfactants can be added to the disclosed compositions, and other dyes, mordanted or otherwise, can be substituted for the hematoxylin. Furthermore, those skilled in the art to which the invention pertains will recognize, or be able to ascertain through no more than routine experimentation, many equivalents to the embodiments described herein. Such equivalents are intended to fall within the scope of the claims.

We claim:

1. A stabilized hematoxylin composition for staining of a tissue or cytology sample, comprising:
   a solvent;
   hematoxylin;
   an amount of a chemical oxidant sufficient to convert at least a portion of the hematoxylin to hematein;
   a mordant;
   a host compound; and
   an antioxidant;
   wherein the host compound is selected from the group consisting of amylose, a cyclodextrin, a cryptand, a cryptophane, a cavitant, a crown ether, a dendrimer, a nanotube, a calixarene, a valinomycin, a nigericin, and combinations thereof.

2. The composition of claim 1, wherein the solvent is an aqueous solvent and the antioxidant is a water-soluble antioxidant.

3. The composition of claim 1, comprising two or more antioxidants.

4. The composition of claim 3, wherein the water soluble antioxidant comprises hydroquinone.

5. The composition of claim 1, wherein the solvent comprises one or more of water, a lower alkanol, and a polyol.

6. The composition of claim 1, wherein the solvent comprises an aqueous solvent, the aqueous solvent comprising water and a polyol.

7. The composition of claim 6, wherein the polyol comprises one or more of glycerol, ethylene glycol, propylene glycol, poly (ethylene glycol), and poly (propylene glycol).

8. The composition of claim 6, wherein the aqueous composition comprises 5-45% by volume of one or more of ethylene glycol and propylene glycol.

9. The composition of claim 8, wherein the aqueous composition comprises 10-30% by volume of one or more of ethylene glycol and propylene glycol.

10. The composition of claim 1, wherein the amount of the chemical oxidant quantitatively oxidizes the hematoxylin to hematein.

11. The composition of claim 1, wherein more than half of the hematoxylin is oxidized to hematein by the chemical oxidant.

12. The composition of claim 1, wherein less than half of the hematoxylin is oxidized to hematein by the chemical oxidant.

13. The composition of claim 1, wherein between 1% and 50% of the hematoxylin is oxidized to hematein by the chemical oxidant.

14. The composition of claim 13, wherein between about 10% and about 30% of the hematoxylin is oxidized to hematein by the chemical oxidant.

15. The composition of claim 1, wherein the chemical oxidant is one or more of sodium iodate, mercuric oxide, potassium permanganate, potassium periodate, and hydrogen peroxide.

16. The composition of claim 1, wherein the chemical oxidant comprises sodium iodate.

17. The composition of claim 1, wherein the mordant comprises one or more of an aluminum mordant, an iron mordant, a bismuth mordant, a copper mordant, a molybdenum mordant, a vanadium mordant, and a zirconium mordant.

18. The composition of claim 1, wherein the mordant comprises an alum.

19. The composition of claim 1, wherein the mordant comprises aluminum sulphate.

20. The composition of claim 1, wherein the host compound is included at concentrations ranging from about 1 mM to about 1 M.

21. The composition of claim 1, wherein the host compound is one or more of a cyclodextrin or a cyclodextrin derivative.

22. The composition of claim 1, wherein the cyclodextrin or cyclodextrin derivative is one or more of β-cyclodextrin and a β-cyclodextrin derivative.

23. The composition of claim 1, wherein the host compound has a water solubility of greater than 100 mg/mL at 25° C.

24. The composition of claim 1, further comprising an acid.

25. The composition of claim 24, wherein the acid comprises acetic acid.

26. The composition of claim 25, wherein no acid is added.

27. The composition of claim 1, wherein the mordant is present in the composition at a concentration greater than a concentration of the hematein in the composition.

28. The composition of claim 1, wherein the mordant is present in the composition at a concentration less than a concentration of the hematein in the composition.

29. The composition of claim 1, comprising a mixture of water and ethylene glycol as the solvent, sodium iodate as the oxidant, aluminum sulphate as the mordant, and β-cyclodextrin or a derivative thereof as the host compound.

30. The composition of claim 29, wherein the mixture of water and ethylene glycol comprises from 10-40% by volume ethylene glycol and from 60-90% water.

31. The composition of claim 1, wherein a molar ratio of hematoxylin to oxidant in the composition is between 6:1 and 1:1.

32. The composition of claim 1, wherein a molar ratio of hematoxylin to mordant in the composition is between 2:1 and 1:100.

33. The composition of claim 32, wherein the molar ratio of hematoxylin to mordant in the composition is between 1:5 and 1:20.

* * * * *